United States Patent
Wiegel et al.

(10) Patent No.: US 12,004,821 B2
(45) Date of Patent: Jun. 11, 2024

(54) SYSTEMS, METHODS, AND DEVICES FOR GENERATING A HYBRID IMAGE

(71) Applicant: Medtronic Navigation, Inc., Louisville, CO (US)

(72) Inventors: Stephanie Elizabeth Wiegel, Lafayette, CO (US); Aditya R. Dalvi, Broomfield, CO (US); Andrew J. Koert, Golden, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 67 days.

(21) Appl. No.: 17/591,904

(22) Filed: Feb. 3, 2022

(65) Prior Publication Data
US 2023/0240756 A1    Aug. 3, 2023

(51) Int. Cl.
| A61B 5/00 | (2006.01) |
| A61B 6/00 | (2006.01) |
| A61B 34/20 | (2016.01) |
| G06T 11/60 | (2006.01) |

(52) U.S. Cl.
CPC ............ *A61B 34/20* (2016.02); *A61B 6/5247* (2013.01); *G06T 11/60* (2013.01); *A61B 2034/2063* (2016.02); *G06T 2210/41* (2013.01)

(58) Field of Classification Search
CPC .................. A61B 34/20; A61B 6/5247; A61B 2034/2063
See application file for complete search history.

(56) References Cited

U.S. PATENT DOCUMENTS

| 5,810,008 A | 9/1998 | Dekel et al. |
| 6,019,724 A | 2/2000 | Gronningsaeter |
| 6,390,982 B1 | 5/2002 | Bova et al. |
| 6,685,644 B2 | 2/2004 | Seo et al. |
| 6,872,179 B2 | 3/2005 | Kamiyama et al. |
| 7,203,277 B2 | 4/2007 | Birkenbach et al. |
| 7,452,357 B2 | 11/2008 | Vlegele et al. |
| 8,116,848 B2 | 2/2012 | Shahidi |
| 9,055,883 B2 | 6/2015 | Tgavalekos et al. |

(Continued)

FOREIGN PATENT DOCUMENTS

| CN | 103777840 | 5/2014 |
| JP | 2011-182983 | 9/2011 |

(Continued)

OTHER PUBLICATIONS

Kim et al. "Feasibility Study of Precise Balloon Catheter Tracking and Visualization with Fast Photoacoustic Microscopy," Sensors, Oct. 2020, vol. 20, No. 19, pp. 5585.

(Continued)

*Primary Examiner* — Joel F Brutus
(74) *Attorney, Agent, or Firm* — Sheridan Ross P.C.

(57) ABSTRACT

Systems, methods, and devices for generating a hybrid image are provided. A preoperative image may be received. A first intraoperative image may be received from an imaging device. The preoperative image and the first intraoperative image may be input into a hybrid model that combines the first intraoperative image with the preoperative image. A hybrid image comprising the preoperative image combined with the first intraoperative image may be generated with an output of the hybrid model.

18 Claims, 6 Drawing Sheets

(56) References Cited

U.S. PATENT DOCUMENTS

| | | |
|---|---|---|
| 9,204,863 B2 | 12/2015 | Kumazawa |
| 9,211,163 B1 | 12/2015 | Jaramaz et al. |
| 9,471,981 B2 | 10/2016 | Arai et al. |
| 9,486,162 B2 | 11/2016 | Zhuang et al. |
| 10,026,191 B2 | 7/2018 | Accomando et al. |
| 10,383,693 B2 | 8/2019 | Schmoll et al. |
| 10,568,535 B2 | 2/2020 | Roberts et al. |
| 10,650,537 B2 | 5/2020 | O'Connor et al. |
| 10,762,341 B2 | 9/2020 | Vilsmeier et al. |
| 11,197,722 B2 | 12/2021 | Tako et al. |
| 2004/0106869 A1 | 6/2004 | Tepper |
| 2005/0085717 A1 | 4/2005 | Shahidi |
| 2005/0261571 A1 | 11/2005 | Willis et al. |
| 2007/0021738 A1 | 1/2007 | Hasser et al. |
| 2007/0239000 A1 | 10/2007 | Emery et al. |
| 2007/0276234 A1 | 11/2007 | Shahidi |
| 2008/0137927 A1 | 6/2008 | Altmann et al. |
| 2013/0158578 A1 | 6/2013 | Ghodke et al. |
| 2014/0066766 A1 | 3/2014 | Stonefield et al. |
| 2015/0130799 A1 | 5/2015 | Holzer et al. |
| 2015/0320395 A1 | 11/2015 | Sato |
| 2016/0150217 A1 | 5/2016 | Popov |
| 2018/0263706 A1* | 9/2018 | Averbuch ............... A61B 6/487 |
| 2018/0303463 A1 | 10/2018 | Zanin et al. |
| 2018/0344411 A1 | 12/2018 | Fahey et al. |
| 2019/0209130 A1 | 7/2019 | Lieblich et al. |
| 2019/0219693 A1 | 7/2019 | Lieblich et al. |
| 2019/0271771 A1 | 9/2019 | Lieblich et al. |
| 2020/0334897 A1 | 10/2020 | Oved |
| 2021/0177524 A1* | 6/2021 | Thienphrapa ............ G06T 11/00 |
| 2021/0192763 A1* | 6/2021 | Liu ...................... H04N 13/106 |
| 2021/0196424 A1 | 7/2021 | Shelton et al. |
| 2021/0386491 A1 | 12/2021 | Shmayahu et al. |

FOREIGN PATENT DOCUMENTS

| | | |
|---|---|---|
| JP | JPWO 2009-136461 | 9/2011 |
| KR | 10-2016-0026598 | 3/2016 |
| WO | WO 2014/174069 | 10/2014 |
| WO | WO 2016/018646 | 2/2016 |
| WO | WO 2016/026053 | 2/2016 |
| WO | WO 2016/082017 | 6/2016 |
| WO | WO 2020/243425 | 12/2020 |

OTHER PUBLICATIONS

Srivastava et al. "Unsupervised Deep Learning based Longitudinal Follicular Growth Tracking during IVF Cycle using 3D Transvaginal Ultrasound in Assisted Reproduction," IEEE, 2021 43rd Annual International Conference of the IEEE Engineering in Medicine & Biology Society (EMBC), Nov. 2021, pp. 3209-3212.

Yeung et al. "ImplicitVol: Sensorless 3D Ultrasound Reconstruction with Deep Implicit Representation," arxiv.org, Sep. 24, 2021, 11 pages.

Invitation to Pay Additional Fees for International (PCT) Patent Application No. PCT/IB2023/050792, dated Apr. 6, 2023, 15 pages.

International Search Report and Written Opinion for International (PCT) Patent Application No. PCT/IB2023/050792, dated May 30, 2023, 21 pages.

International Search Report and Written Opinion for International (PCT) Patent Application No. PCT/IB2023/050646, dated May 15, 2023, 10 pages.

International Search and Written Opinion for International (PCT) Patent Application No. PCT/IB2023/050675, dated Apr. 26, 2023, 11 pages.

International Search Report and Written Opinion for International (PCT) Patent Application No. PCT/IB2023/050678, dated Apr. 24, 2023, 14 pages.

U.S. Appl. No. 17/591,904, filed Feb. 3, 2022.
U.S. Appl. No. 17/591,919, filed Feb. 3, 2022.
U.S. Appl. No. 17/591,951, filed Feb. 3, 2022.
U.S. Appl. No. 17/591,974, filed Feb. 3, 2022.
Official Action for U.S. Appl. No. 17/591,951, dated Nov. 16, 2023 72 pages.

* cited by examiner

SYSTEMS, METHODS, AND DEVICES FOR GENERATING A HYBRID IMAGE

FIELD

The present technology generally relates to imaging and image processing, and relates more particularly to hybrid imaging.

BACKGROUND

Imaging devices may be used by a medical provider for diagnostic and/or therapeutic purposes. Images may be obtained from imaging devices using different modalities at various times (e.g., preoperatively, intraoperatively, postoperatively). Such images may also contain various information (e.g., soft tissue and/or hard tissue) based on the nature of the imaging device used to capture the images.

SUMMARY

Example aspects of the present disclosure include:

A system for generating a hybrid image according to at least one embodiment of the present disclosure comprises an imaging device; a processor; and a memory storing data for processing by the processor, the data, when processed, causing the processor to: receive a preoperative image; receive a first intraoperative image from the imaging device; input the preoperative image and the first intraoperative image into a hybrid model, the hybrid model configured to combine the first intraoperative image with the preoperative image; and generate, with an output of the hybrid model, a hybrid image comprising the preoperative image combined with the first intraoperative image.

Any of the aspects herein, wherein the preoperative image comprises an x-ray image and the first intraoperative image comprises an ultrasound image.

Any of the aspects herein, wherein the memory stores further data for processing by the processor that, when processed, causes the processor to: receive a second intraoperative image; input the preoperative image and the second intraoperative image into the hybrid model; and generate, with an output of the hybrid model, an updated hybrid image comprising the preoperative image and the second intraoperative image, wherein the second intraoperative image replaces the first intraoperative image.

Any of the aspects herein, wherein the preoperative image, the first intraoperative image, and the second intraoperative image each depict at least one anatomical element, wherein the memory stores further data for processing by the processor that, when processed, causes the processor to: detect movement in the at least one anatomical element based on a difference in the first intraoperative image and the second intraoperative image; and replace the first intraoperative image with the second intraoperative image when movement is detected.

Any of the aspects herein, wherein the memory stores further data for processing by the processor that, when processed, causes the processor to: generate a preoperative three-dimensional representation of one or more anatomical elements using the preoperative image; generate a three-dimensional representation of an anatomical element using the first intraoperative image; and combine the preoperative three-dimensional representation with the three-dimensional representation.

Any of the aspects herein, further comprising a navigation system configured to use the hybrid image for navigation of at least one surgical instrument, wherein the memory stores further data for processing by the processor that, when processed, causes the processor to: generate instructions for navigating the at least one surgical instrument based on the hybrid image.

Any of the aspects herein, wherein the memory stores further data for processing by the processor that, when processed, causes the processor to: generate a three-dimensional representation based on the first intraoperative image and pose information of the imaging device received from the navigation system, the pose information correlating to one or more poses of the imaging device when the first intraoperative image was obtained.

Any of the aspects herein, wherein generating the hybrid image comprises at least one of merging the first intraoperative image with the preoperative image or overlaying the first intraoperative image onto the preoperative image.

Any of the aspects herein, wherein the hybrid model is trained using historical preoperative images and historical intraoperative images.

Any of the aspects herein, wherein the preoperative image comprises hard tissue information and the first intraoperative image comprises soft tissue information, wherein a first set of pixels represents the hard tissue information and a second set of pixels represents the soft tissue information.

A device for generating a hybrid image according to at least one embodiment of the present disclosure comprises a processor; and a memory storing data for processing by the processor, the data, when processed, causing the processor to: receive a preoperative image; receive a first intraoperative image; input the preoperative image and the first intraoperative image into a hybrid model, the hybrid model configured to combine the first intraoperative image with the preoperative image; and generate, with an output of the hybrid model, a hybrid image comprising the preoperative image and the first intraoperative image Any of the aspects herein, wherein the preoperative image comprises an x-ray image and the first intraoperative image comprises an ultrasound image.

Any of the aspects herein, wherein the memory stores further data for processing by the processor that, when processed, causes the processor to: receive a second intraoperative image; input the preoperative image and the second intraoperative image into the hybrid model; and generate an updated hybrid image comprising the preoperative image and the second intraoperative image.

Any of the aspects herein, wherein the preoperative image, the first intraoperative image, and the third intraoperative image each depict at least one anatomical element, wherein the memory stores further data for processing by the processor that, when processed, causes the processor to: detect movement in the at least one anatomical element based on a difference in the first intraoperative image and the second intraoperative image.

Any of the aspects herein, wherein the memory stores further data for processing by the processor that, when processed, causes the processor to: generate a preoperative three-dimensional representation of one or more anatomical elements using the preoperative image; generate a three-dimensional representation of an anatomical element using the first intraoperative image; and combine the three-dimensional representation with the preoperative three-dimensional representation.

Any of the aspects herein, wherein the memory stores further data for processing by the processor that, when processed, causes the processor to: generate a three-dimensional volume based on the first intraoperative image and pose information of the imaging device received from the navigation system, the pose information correlating to one or more poses of the imaging device when the first intraoperative image was obtained.

Any of the aspects herein, wherein generating the hybrid image comprises at least one of merging the first intraoperative image with the preoperative image or overlaying the first intraoperative image onto the preoperative image.

Any of the aspects herein, wherein the hybrid model is trained using historical preoperative images and historical intraoperative images.

Any of the aspects herein, wherein the preoperative image comprises hard tissue information and the first intraoperative image comprises soft tissue information.

A system for navigating using a hybrid image according to at least one embodiment of the present disclosure comprises an imaging device; a navigation system; a processor; and a memory storing data for processing by the processor, the data, when processed, causing the processor to: receive a preoperative image; receive an intraoperative image from the imaging device; input the preoperative image and the first intraoperative image into a hybrid model, the hybrid model configured to combine the first intraoperative image with the preoperative image; generate, with the output of the hybrid model, a hybrid image comprising the preoperative image and the first intraoperative image; and navigate, by the navigation system, at least one instrument using the hybrid image.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided herein below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions or algorithms may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10x Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Navigation systems may be used to provide navigation for a surgeon or a robotic system during a surgical procedure. Such systems may provide navigation relative to, for example, a preoperative image (e.g., a magnetic resonance image (MRI) or computed tomography (CT) image) depicting one or more anatomical elements. However, during a surgical procedure, if the one or more anatomical elements move or shift, then the navigation system may no longer be accurate and may require updating.

According to at least one embodiment of the present disclosure, ultrasound imaging can be used with the navigation system to provide updated imaging of the one or more anatomical elements, which can provide updated information about a pose of the one or more anatomical elements. The pose includes a position and an orientation. The updated images may also be aligned with the preoperative image. Thus, integration of ultrasound and navigation can provide real-time updated imaging of one or more anatomical elements to ensure that the navigation system is navigating relative to a current pose of the one or more anatomical elements.

There are also a number of advantages that combining ultrasound imaging with surgical navigation can offer. Ultrasound does not emit harmful radiation and thus, can be used continuously during a surgical procedure without exposing a patient and a surgical team to radiation. This results in a safer environment for the patient, surgeon, and surgical team. Ultrasound may also be helpful to track certain objects and/or anatomical elements (e.g., soft tissue) as compared to, for example, X-ray based imaging, which may be better suited for other objects/anatomical elements (e.g., hard tissue, manmade objects, etc.). Ultrasound with navigation can be used for multiple applications such as, for example, cranial and/or spinal procedures. Current imaging and navigation can overlay an ultrasound image over a pre-operative image (e.g., an MRI or CT image); take measurements on ultrasound images; and/or capture a series of images and play through the images.

In at least one embodiment, ultrasound navigation may be used for, for example, three-dimensional ultrasound navigation; electromagnetic navigated ultrasound; augment reality; using artificial intelligence to merge ultrasound with pre-operative imaging for real-time brain shift compensation; reconstructing patient anatomy of interest (e.g., vascular and/or tumor); patient auto-registration; tumor ablation confirmation; tracking hardening of biologics; track size of tool (e.g., a balloon) between anatomical elements (e.g., vertebrae); and/or segmental tracking.

Embodiments of the present disclosure provide technical solutions to one or more of the problems of (1) updating a pose of one or more anatomical elements during a surgical procedure; (2) tracking and compensating for movement of one or more anatomical elements during a surgical procedure; (3) providing real-time updates of a pose of one or more anatomical elements to a navigation system; (4) providing/updating navigation path(s) after movement of one or more anatomical elements; and (5) increasing patient, surgeon, and surgeon team safety.

Figure 1:
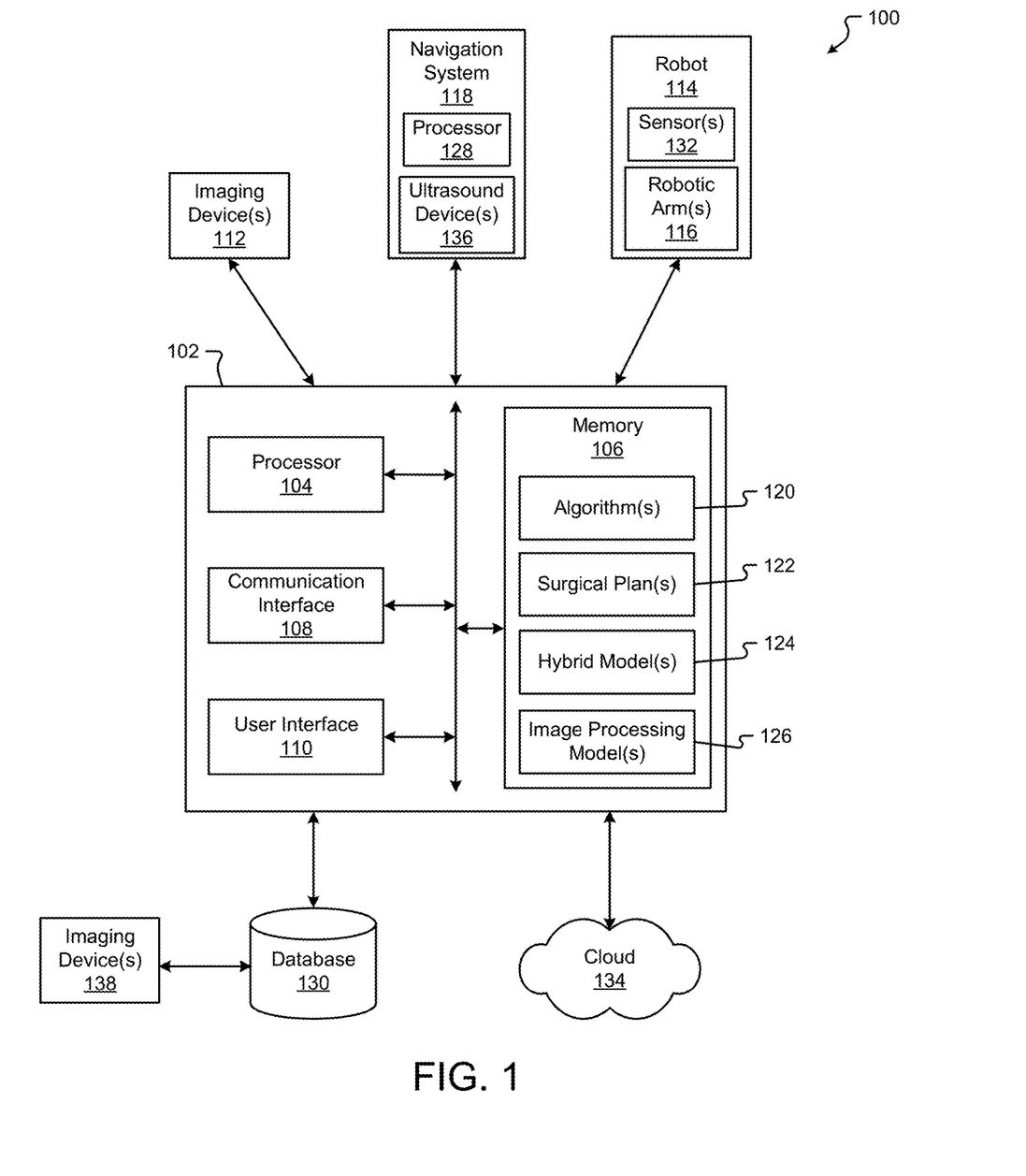
FIG. 1 is a block diagram of a system according to at least one embodiment of the present disclosure.

Turning first to FIG. 1, a block diagram of a system 100 according to at least one embodiment of the present disclosure is shown. The system 100 may be used to generate a hybrid image or multiple hybrid images, which may be used for robot navigation during the surgical procedure, and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 400, 500, 600, 700 described herein, or of any other methods. The memory 106 may store, for example, one or more algorithms 120, one or more surgical plans 122, one or more hybrid model(s) 124, and/or one or more image processing model(s) 126. Such algorithms may, in some embodiments, be organized into one or more applications, modules, packages, layers, or engines. Alternatively or additionally, the memory 106 may store other types of data (e.g., machine learning models, artificial neural networks, etc.) that can be processed by the processor 104 to carry out the various method and features described herein. Thus, although various components of memory 106 are described as algorithms, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. The imaging device 112 may be capable of capturing a two-dimensional image, a series of two-dimensional images, a three-dimensional image, and/or a series of three-dimensional images to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient.

In some embodiments, the imaging device 112 may comprise more than one imaging device 112. For example, a first imaging device may provide first image data and/or a first image at a first time, and a second imaging device may provide second image data and/or a second image at the first time or at a second time after the first time. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

In some embodiments, the imaging device 112 may comprise a source and a detector. In such embodiments, the imaging device 112 may be an ultrasound device or an x-ray imaging device. In some embodiments, the source and the detector may be in separate housings or are otherwise physically separated. In such embodiments, the source may be oriented by a first robotic arm and the detector may be oriented by a second robotic arm, as will be described in more detail below. In other embodiments, the source and the detector may be in the same housing. The source may be configured to emit a wave and the detector may be configured to receive a signal indicative of the emitted wave. The detector may also be configured to save a plurality of image datasets to, for example, the memory 106.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure.

The robot 114 may comprise one or more robotic arms 116. The robotic arms may be controlled in a single, shared coordinate space, or in separate coordinate spaces. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components such as, for example, the source and the detector, one robotic arm 116 may hold the source, and another robotic arm 116 may hold the detector. Each robotic arm 116 may be accurately positionable independently of the other robotic arm (e.g., the detector can be positioned or oriented independently of the source). In some embodiments, one robotic arm 116 may orient the source at a first pose across from the detector oriented by another robotic arm 116 at a second pose. In some embodiments, the source may remain at the same pose while the detector is oriented at different poses. In other embodiments, the detector may remain at the same pose while the source is oriented at different poses. In still other embodiments, both the detector and the source may each be oriented at different poses.

The robot 114, together with the robotic arm 116, may have, for example, one, two, three, four, five, six, seven, or more degrees of freedom. Further, the robotic arm 116 may be positioned or positionable in any pose, plane, and/or focal point. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

In some embodiments, electromagnetic sensor(s) may be used to track any component of the system 100 including, for example, the imaging device 112. The electromagnetic sensor(s) may be used by the navigation system 118 to track a corresponding component. For example, an electromagnetic sensor may be disposed on or integrated with an ultrasound transducer for tracking a pose of the transducer in real-time. In some embodiments, the electromagnetic sensor may be removable.

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker or an electromagnetic sensor attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

In some embodiments, an ultrasound device 136 may be integrated with the navigation system 118 in which images from the ultrasound device may be used by the navigation system 118 for navigation. In some embodiments, the hardware for an ultrasound device 136 may be directly integrated with the navigation system 118 hardware. In other embodiments, the ultrasound device 136 may be a separate component. Whether directly integrated or combined as separate components, a processor such as the processor 104 or a processor 128 of the navigation system 118 may receive data from the ultrasound device 136 and automatically process such data for use by the navigation system 118.

In embodiments using an integrated navigation system 118 and ultrasound device 136, the navigation system 118 may navigate a surgeon or robotic system relative to a preoperative image (e.g., MRI or CT image(s)) depicting one or more anatomical elements, and an ultrasound probe may provide real-time or live imaging of the one or more anatomical elements during a surgical procedure. The preoperative image(s) may be obtained from, for example, the database 130 and/or the second imaging device 138. The real-time or live image(s) obtained from the ultrasound device 136 can be aligned with preoperative image(s) (e.g., MRI or CT images) to confirm or—in instances where an anatomical element has moved—update a pose of the anatomical element and surrounding anatomical elements. The navigation system 118 may then provide navigation based on the updated pose of the anatomical element(s). Thus, the ultrasound device 136 enables the navigation system 118 to continue to navigate when one or more anatomical elements shift or move, either in space or relative to one another. In some instances, the real-time or live image(s) can be used to generate a three-dimensional ultrasound representation that can be overlaid onto a preoperative three-dimensional representation generated from preoperative image(s). The navigation system 118 may then navigate based on the three-dimensional ultrasound representation. In some instances, the real-time or live image(s) can be used to generate a three-dimensional ultrasound representation that can be overlaid onto a preoperative two-dimensional image that depicts the anatomical elements.

The combined navigation system 118 and ultrasound device 136 may be used in various applications. For example, the combined navigation system 118 and ultrasound device 136 may be used to view a progress of or confirm a tumor ablation, while the tumor is in the process of being ablated. In such examples, a navigated ultrasound probe may be used to obtain a current ultrasound image of an ablated tumor area, which may be compared to a preoperative image obtained prior to the ablation procedure. In another example, the combined navigation system 118 and ultrasound device 136 may be used to auto-register and/or reregister a patient. In such examples, images obtained from the ultrasound device 136 may be automatically aligned and correlated to preoperative images. In still another example, the combined navigation system 118 and ultrasound device 136 may be used generate a three-dimensional representation of one or more anatomical elements based on a set of images and corresponding pose information that can be used by the navigation system 118 for navigation, as will be described in detail in FIGS. 3-5.

The database 130 may store, for example, the one or more algorithms 120, the one or more surgical plans 122 (including, for example, preoperative image(s); steps for orienting the imaging device 112 at one or more poses; etc.); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the model architecture 200 and/or methods 400, 500, 600, 700 described herein. The system 100 or similar systems may also be used for other purposes.

Figure 2:
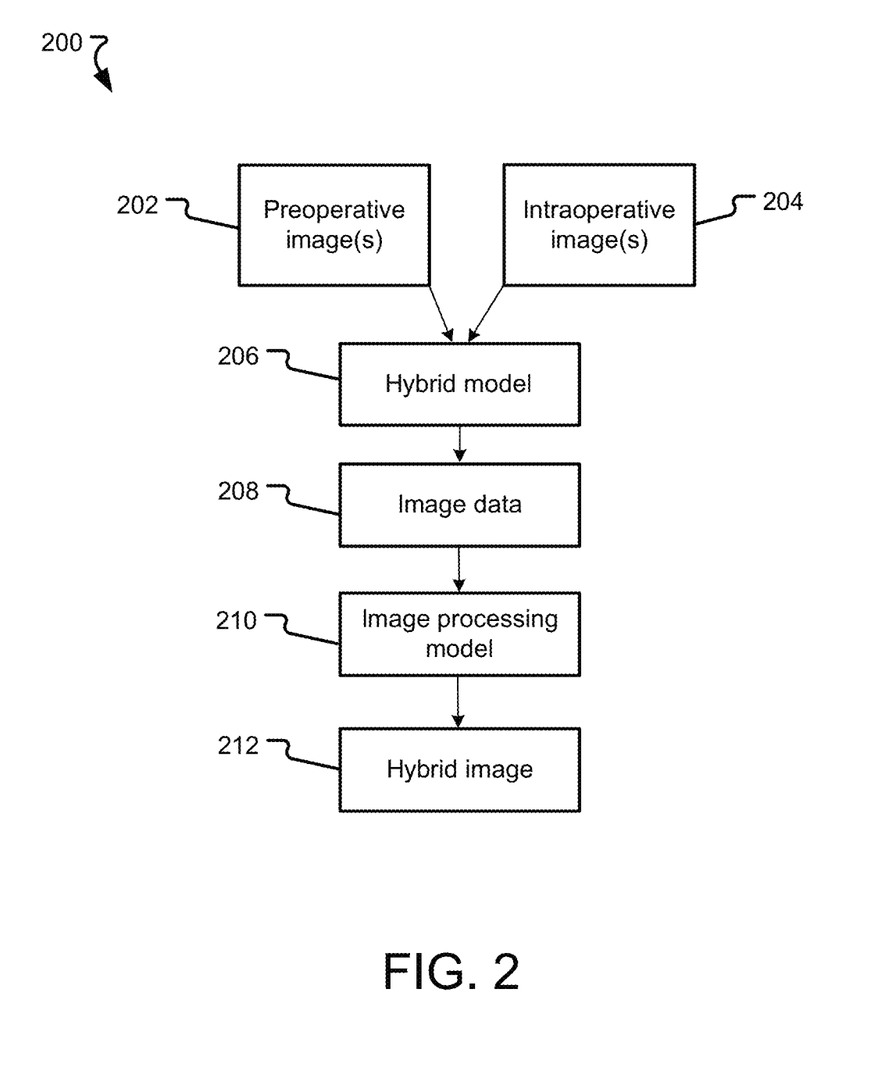
FIG. 2 is a flowchart according to at least one embodiment of the present disclosure.

Turning to FIG. 2, an example of a model architecture 200 that supports methods and systems (e.g., Artificial Intelligence (AI)-based methods and/or system) for generating a hybrid image is shown.

Preoperative image(s) 202 and intraoperative image(s) 204 may each be obtained by an imaging device such as the imaging device 112 or by different imaging devices 112 (e.g., preoperative images 202 may be obtained from the second imaging device 138 or a database 130 storing images previously obtained from the second imaging device 138 whereas intraoperative images 204 may be obtained from the imaging device 112 or the ultrasound device 136. In some embodiments an imaging device that obtains the preoperative image 202 may be different than an imaging device that obtains the intraoperative image 204. For example, the imaging device that obtains the preoperative image 202 may be a CT scanner or an MRI scanner and the imaging device that obtains the intraoperative image 204 may be an ultrasound device. Each of the preoperative image 202 and the intraoperative image 204 may depict one or more objects and/or one or more anatomical elements of, for example, a patient. The preoperative image 202 may be obtained prior to a surgical procedure and the intraoperative image 204 may be obtained during the surgical procedure. When different imaging devices 112 are used to obtain preoperative images 202 and intraoperative images 204, it should be appreciated that different types of information may be represented in the different images. For instance, the preoperative images 202 may contain more information or details (e.g., pixel contrast) showing hard tissue or objects that are recognized using a first imaging technique (e.g., a magnetic-resonant imaging technique, a radiation imaging technique, etc.) whereas the intraoperative images 204 may contain more information or details (e.g., pixel contrast) showing soft tissue or objects that are recognized using a second imaging technique (e.g., an ultrasonic imaging technique, a Lidar imaging technique, etc.).

The preoperative image 202 and the intraoperative image 204 are received as input at the computer device 102, which may reference a machine learning model stored in memory 106, such as a hybrid model 206, 124. The hybrid model 206 may be trained using historical preoperative image(s) and/or historical intraoperative image(s). In other embodiments, the hybrid model 206 may be trained using the preoperative image 202 and the intraoperative image 204. In such embodiments, the hybrid model 206 may be trained prior to inputting the preoperative image 202 and the intraoperative image 204 into the hybrid model 206 or may be trained in parallel with inputting the preoperative image 202 and the intraoperative image 204. The hybrid model 206 may be configured to generate image data 208 for a hybrid image comprising image data of the preoperative image 202 and the intraoperative image 204.

The image data 208 may be used by a processor such as the processor 104 as input for an image processing model 210, 126. The image processing model 210 may output a hybrid image 212, which may comprise some or all information from the preoperative image 202 and some or all information from the intraoperative image 204 overlaid, integrated, merged, or otherwise combined with each other. The image processing model 210 may be trained using historical image data. In other embodiments, the image processing model 210 may be trained using the image data 208. In such embodiments, the image processing model 210 may be trained prior to inputting the image data 208 into the image processing model 210 or in parallel with inputting the image data 208 into the image processing model 210.

Figure 3:
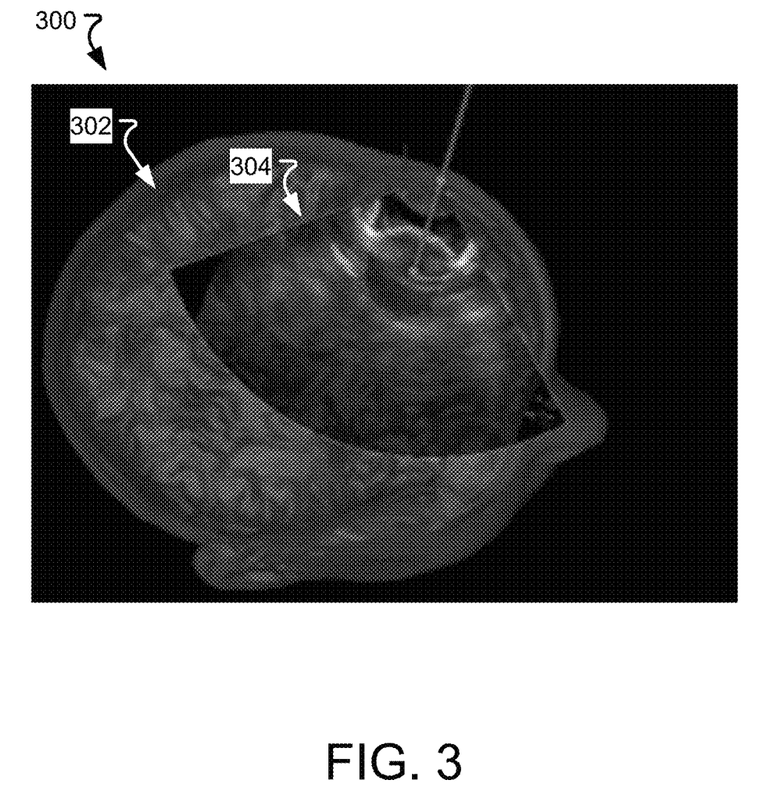
FIG. 3 is an example illustration of a hybrid image according to at least one embodiment of the present disclosure.

Turning to FIG. 3, an example illustration of a hybrid image 300 is shown. The hybrid image 300 may be the same as the hybrid image 212 received as an output from the image processing model 210. As shown, the hybrid image 300 may comprise a preoperative image 302 (which may be the same as or similar to the preoperative image 202) and an intraoperative image 304 (which may be the same as or similar to the intraoperative image 204 combined. In the illustrated image, the preoperative image 302 comprises an MRI scan of a patient brain and the intraoperative image 204 comprises one or more ultrasound images of a portion of the brain. The intraoperative image 204 may comprise a plurality of ultrasound images that may show, for example, movement such as a shift of the brain. Thus, the hybrid image 300 may be used to track and detect, for example, brain shift of a patient during a surgical procedure.

Figure 4:
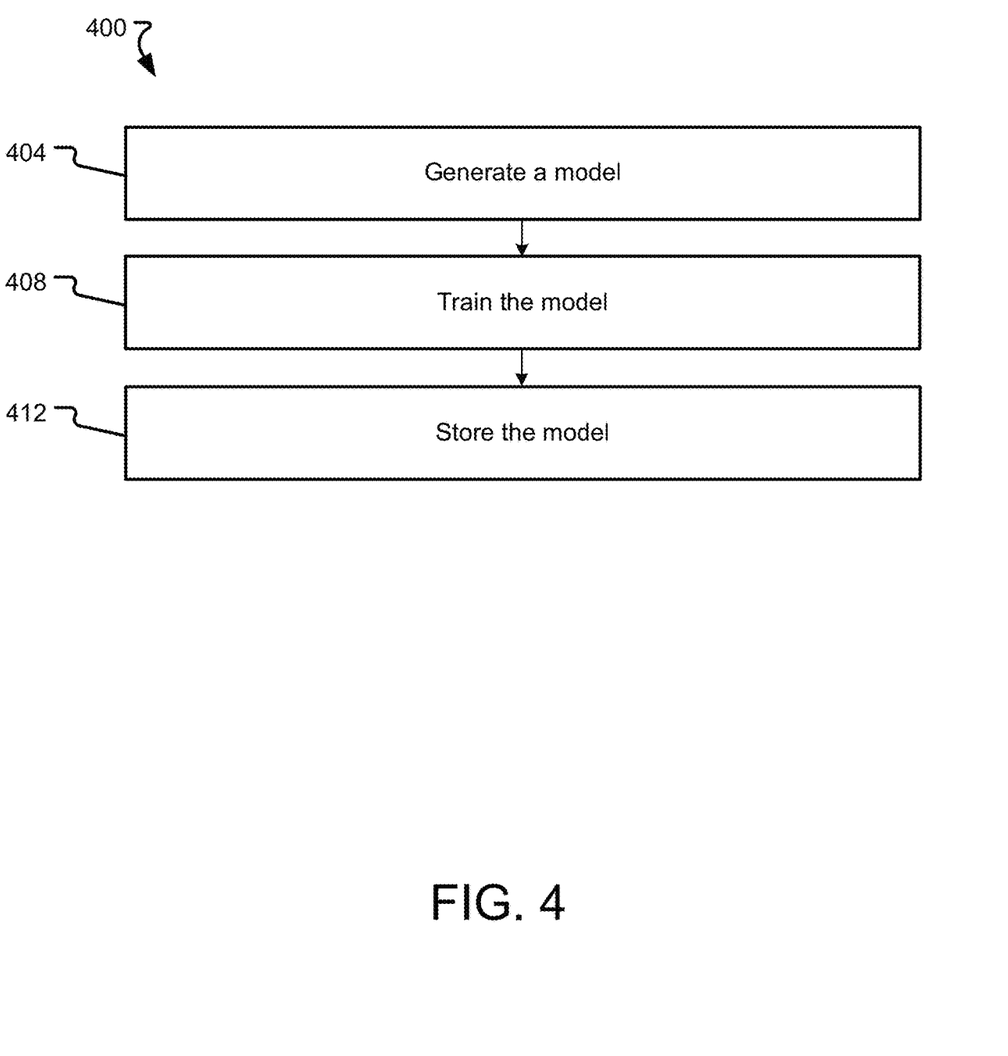
FIG. 4 is a flowchart according to at least one embodiment of the present disclosure.

Turning to FIG. 4, a method 400 that may be used, for example, for generating a model is provided.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 210. The at least one processor may perform the method 210 by executing instructions stored in a memory such as the memory 106. The instructions may correspond to one or more steps of the method 210 described below. The instructions may cause the processor to execute one or more algorithms, such as the algorithm 120.

The method 400 comprises generating a model (step 404). The model may be the reconstruction model 206, 124. A processor such as the processor 104, 128 may generate the model. The model may be generated to facilitate and enable, for example, generating of a three-dimensional representation of one or more anatomical elements and/or objects.

The method 400 also comprises training the model (step 408). In embodiments where the model is trained prior to a surgical procedure, the model may be trained using historical data from a number of patients. In some embodiments, the historical data may be obtained from patients that have similar patient data to a patient on which a surgical procedure is to be performed. In other embodiments, the historical data may be obtained from any patient.

In other embodiments, the model may be trained in parallel with use of another model. Training in parallel may, in some embodiments, comprise training a model using input received during, for example, or prior to a surgical procedure, while also using a separate model to receive and act upon the same input. Such input may be specific to a patient undergoing the surgical procedure. In some instances, when the model being trained exceeds the model in use (whether in efficiency, accuracy, or otherwise), the model being trained may replace the model in use. Such parallel training may be useful, for example, in situations, where a model is continuously in use (for example, when an input (such as, for example, an image) is continuously updated) and a corresponding model may be trained in parallel for further improvements.

In some embodiments, it will be appreciated that the model trained using historical data may be initially used as a primary model at a start of a surgical procedure. A training model may also be trained in parallel with the primary model using patient-specific input until the training model is sufficiently trained. The primary model may then be replaced by the training model.

The method 400 also comprises storing the model (step 412). The model may be stored in memory such as the memory 106 for later use. In some embodiments, the model is stored in the memory when the model is sufficiently trained. The model may be sufficiently trained when the model produces an output that meets a predetermined threshold, which may be determined by, for example, a user, or may be automatically determined by a processor such as the processor 104, 128.

The present disclosure encompasses embodiments of the method 400 that comprise more or fewer steps than those described above, and/or one or more steps that are different than the steps described above.

Figure 5:
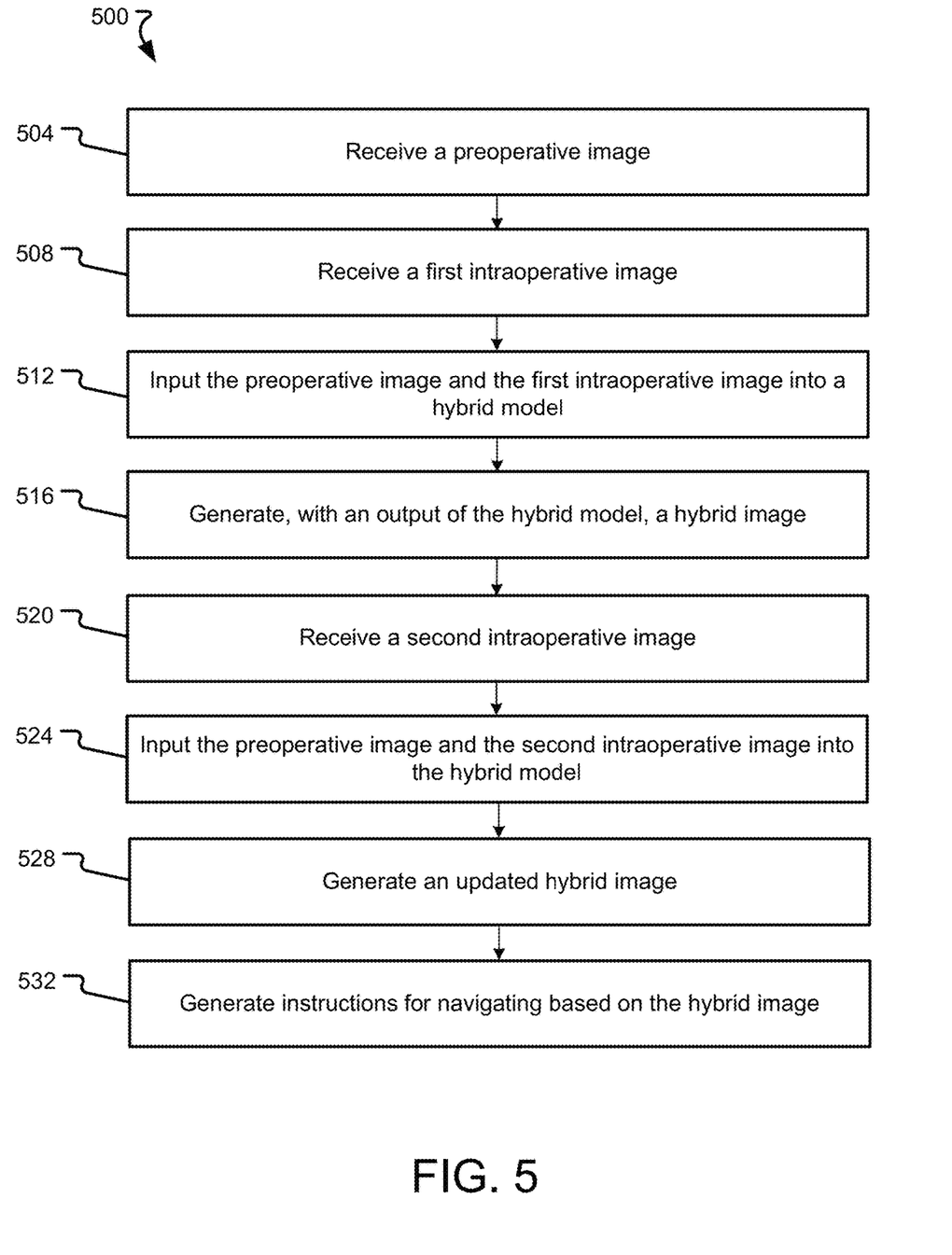
FIG. 5 is a flowchart according to at least one embodiment of the present disclosure.

FIG. 5 depicts a method 500 that may be used, for example, for generating a hybrid image.

The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 500. The at least one processor may perform the method 500 by executing instructions stored in a memory such as the memory 106. The instructions may correspond to one or more steps of the method 500 described below. The instructions may cause the processor to execute one or more algorithms, such as the algorithm 120.

The method 500 comprises receiving a preoperative image (step 504). The preoperative image may be the same as or similar to the preoperative image 202. The preoperative image may be obtained from an imaging device such as the imaging device 148 and/or a database such as the database 140. In some embodiments, the imaging device is a CT scanner or an MRI scanner. The preoperative image may comprise one or more two-dimensional images, one or more three-dimensional images, or a combination of one or more two-dimensional images and one or more three-dimensional images. In some embodiments, the preoperative image may be obtained from a surgical plan such as the surgical plan 122. In other embodiments, the preoperative image may be received via a user interface such as the user interface 110 and/or via a communication interface such as the communication interface 108 of a computing device such as the computing device 102, and may be stored in a memory such as the memory 106. The image data may also be generated by and/or uploaded to any other component of the system 100. In some embodiments, the preoperative image may be indirectly received via any other component of the system 100 or a node of a network to which the system 100 is connected.

The preoperative image may depict one or more anatomical elements. In some embodiments, the preoperative image may contain hard tissue information about the one or more anatomical elements. In other embodiments, the preoperative image may contain soft tissue information about the one or more anatomical elements.

The method 500 also comprises receiving a first intraoperative image (step 508). The first intraoperative image may be the same as or similar to the intraoperative image 204. The intraoperative image may be obtained from an imaging device such as the imaging device 112. In some embodiments, the imaging device is an ultrasound device. In such embodiments where the imaging device is an ultrasound device, the first intraoperative image may be a two-dimensional image. Further, in such embodiments, multiple two-dimensional image(s) may be taken to form or generate a three-dimensional representation of one or more anatomical elements, as will be described with respect to FIG. 6.

The first intraoperative image may depict one or more anatomical elements. The one or more anatomical elements depicted in the first intraoperative image may be the same as the one or more anatomical elements depicted in the preoperative image. In other instances, the first intraoperative image may depict at least one of the one or more anatomical elements depicted in the preoperative image. In some embodiments, the first intraoperative image may contain soft tissue information about the one or more anatomical elements.

The method 500 also comprises inputting the preoperative image and the first intraoperative image into a hybrid model (step 512). The hybrid model may be the same as or similar to the hybrid model 206. The hybrid model may be configured to combine the first intraoperative image and preoperative image. In some embodiments, the hybrid model may output image data such as the image data 208. The hybrid model may be trained using historical preoperative image(s) and/or historical intraoperative image(s). In some embodiments, the historical preoperative image(s) and/or historical intraoperative image(s) may depict one or more anatomical elements similar to the one or more anatomical elements depicted by the preoperative image and/or the intraoperative image.

The method 500 also comprises generating, with an output of the hybrid model, a hybrid image (step 516). In some embodiments, the output of the hybrid model may be the image data, which may be processed by an image processing model such as the image processing model 210. The image processing model may be configured to generate and output the hybrid image. The hybrid image may comprise the preoperative image and the first intraoperative image overlaid, integrated, merged, or otherwise combined with each other. In some embodiments, the first intraoperative image may be overlaid onto the preoperative image.

In some embodiments, the preoperative image comprises hard tissue information and the first intraoperative image comprises soft tissue information. In such embodiments, the hybrid information comprises the hard tissue information and the soft tissue information combined. The hard tissue information may be obtained from, for example, an x-ray image and the soft tissue information may be obtained from, for example, an ultrasound image. The hard tissue information may be represented by a first set of pixels and the soft tissue information may be represented by a second set of pixels. In some instances, the first set of pixels may have a saturation greater than the second set of pixels. In other instances, the first set of pixels may contrast with the second set of pixels. By combining the hard tissue information and the soft tissue information, the combined information may be presented to a user in a form that is succinct and easy to understand.

In some embodiments, the preoperative image comprises an x-ray image and the first intraoperative image comprises an ultrasound image. In such embodiments, the ultrasound image may be overlaid on the x-ray image. In some embodiments, as the intraoperative image changes, such changes may be presented in real-time or near real-time to a user such as a surgeon or medical provider. For example, soft tissue information obtained from the ultrasound image such as tissue may change throughout a procedure (e.g., ablation, cutting, drilling, etc.) and such changes in the tissue may be viewable in the hybrid image.

The method 500 also comprises receiving a second intraoperative image (step 520). The step 520 may be the same as or similar to the step 508. The second intraoperative image may be obtained from the same imaging device as the first intraoperative image. In such embodiments, the imaging device may obtain the first intraoperative image at a first pose and the second intraoperative image at a second pose. The first pose may be the same as or different from the second pose.

The method 500 also comprises inputting the preoperative image and the second intraoperative image into the hybrid model (step 524). The step 524 may be the same as or similar to the step 512.

The method 500 also comprises generating an updated hybrid image (step 528). The step 528 may be the same as or similar to the step 516. In some embodiments, the second intraoperative image may replace the first intraoperative image in the updated hybrid image.

It will be appreciated that in some embodiments, the steps 520, 524, and/or 528 may be continuously repeated to provide real-time updates regarding a pose of the one or more anatomical elements. In other words, an intraoperative image may be obtained continuously, and in some instances, the subsequent intraoperative image may be inputted into the hybrid model to continuously generate image data for an updated hybrid image. In other instances, the subsequent intraoperative image may be compared to the prior intraoperative image, and if a change is detected, the subsequent intraoperative image may be inputted into the hybrid model to generate image data for an updated hybrid image. It will also be appreciated that in some embodiments, an intraoperative image may be obtained at a time interval.

The method 500 also comprises generating instructions for navigating based on the hybrid image (step 532). A navigation system such as the navigation system 118 may provide the navigation. The instructions may be generated for navigating one or more instruments, tools, and/or anatomical elements, by a user such as a surgeon or other medical provide or by a robotic arm such as the robotic arm 116. The instructions may be generated by a processor such as the processor 104 (whether of the navigation system or as a separate component). The instructions may be machine readable data and transmitted to, for example, the robotic arm 116 to cause the robotic arm 116 to execute the instructions. The instructions may also be human readable data and may be displayed on a user interface such as the user interface 110 for instructing the user.

The present disclosure encompasses embodiments of the method 500 that comprise more or fewer steps than those described above, and/or one or more steps that are different than the steps described above.

Figure 6:
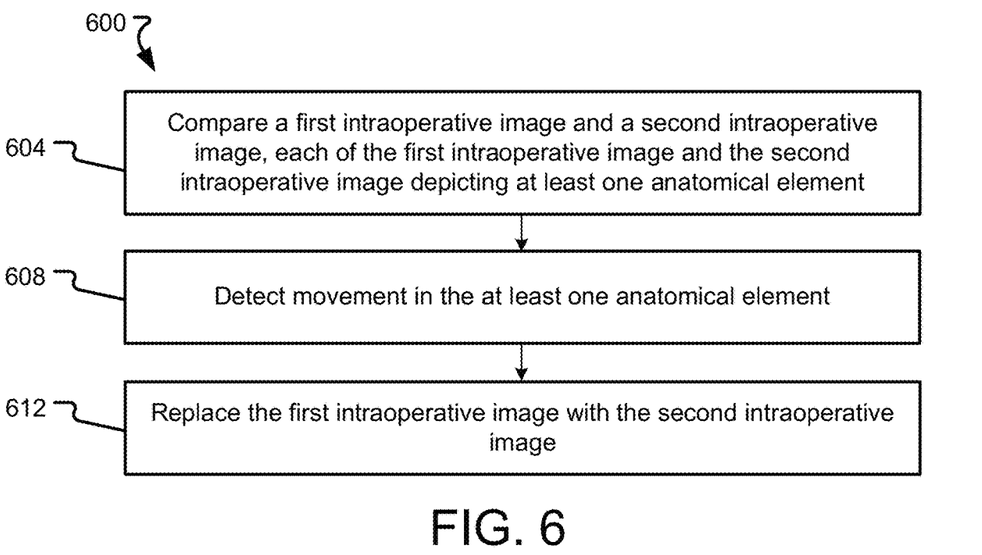
FIG. 6 is a flowchart according to at least one embodiment of the present disclosure.

FIG. 6 depicts a method 600 that may be used, for example, for detecting movement of one or more anatomical elements and/or one or more objects.

The method 600 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 600. The at least one processor may perform the method 600 by executing instructions stored in a memory such as the memory 106. The instructions may correspond to one or more steps of the method 600 described below. The instructions may cause the processor to execute one or more algorithms, such as the algorithm 120.

The method 600 comprises comparing a first intraoperative image and a second intraoperative image (step 604). Each of the first intraoperative image and the second intraoperative image may be the same as or similar to the intraoperative image 204. The first intraoperative image and the second intraoperative image may be received in a step similar to or the same as the steps 608 and 520 of method 600 described above. The first intraoperative image and the second intraoperative image may depict one or more anatomical elements.

Comparing the first intraoperative image and the second intraoperative image may comprise aligning the first intraoperative image and the second intraoperative image and detecting any changes between the two images. In such embodiments, the first intraoperative image and the second intraoperative image may be obtained from the imaging device at the same pose. In other embodiments, the first intraoperative image and the second intraoperative image may be obtained from the imaging device at a first pose and a second pose, respectively. The first pose may be different from the second pose. In such embodiments, the one or more anatomical elements depicted in the first intraoperative image may be aligned with the one or more anatomical elements depicted in the second intraoperative image and changes may be detected between one or more anatomical elements depicted in the two images.

The method 600 also comprises detecting movement in the at least one anatomical element (step 608). Movement may be detected when the first intraoperative image does not match the second intraoperative image, or when the one or more anatomical elements depicted in the first intraoperative image do not match the one or more anatomical elements depicted in the second intraoperative image. Such mismatch (in any instances) may suggest that at least one anatomical element of the one or more anatomical elements has moved or shifted. For example, in a cranial surgical procedure, a brain shift may occur. In such examples, the brain shift may be represented by a shift in a position of the brain as depicted in the first intraoperative image to the second intraoperative image (or any subsequent intraoperative image). In other examples, any anatomical element, instrument, or tool may be tracked for movement.

A pose, position, or orientation of an anatomical element may be updated in a preoperative image or three-dimensional representation when movement is detected. Such preoperative image or three-dimensional representation may be used by a navigation system such as the navigation system 118 for providing navigation for a user or a robot such as the robot 115. By updating such pose, position, or orientation of an anatomical element, the navigation system may continuously and seamlessly provide navigation even as anatomical elements move throughout a procedure. More specifically, a change in a pose, position, or orientation of an anatomical element can be tracked and compensated for by the navigation system. Further, the navigation system may be able to generate instructions for, for example, repositioning an imaging device that may be used to track an anatomical element. For example, an imaging device may be used to track a patient brain. If the brain shifts, the navigation system may instruct a user or a robot arm such as the robotic arm 116 to shift the imaging device such that the brain remains within a field of view of the imaging device.

The method 600 also comprises replacing the first intraoperative image with the second intraoperative image (step 612). In some embodiments, where movement is detected as in, for example, step 608, the first intraoperative image may be replaced with the second intraoperative image. In such embodiments, the steps 524 and 528 of method 600 described above may be executed to input the second intraoperative image into a hybrid model such as the hybrid model 206 and an updated hybrid image may be generated using the output of the hybrid model. The updated hybrid image may replace the first intraoperative image with the second intraoperative image. In other embodiments, the first intraoperative image may be replaced with the second intraoperative image regardless of whether movement is detected. In still other embodiments, when movement is not detected, the first intraoperative image may not be replaced with the second intraoperative image. In such embodiments, the second intraoperative image may be saved to, for example, a memory such as the memory 106, or discarded.

The present disclosure encompasses embodiments of the method 600 that comprise more or fewer steps than those described above, and/or one or more steps that are different than the steps described above.

Figure 7:
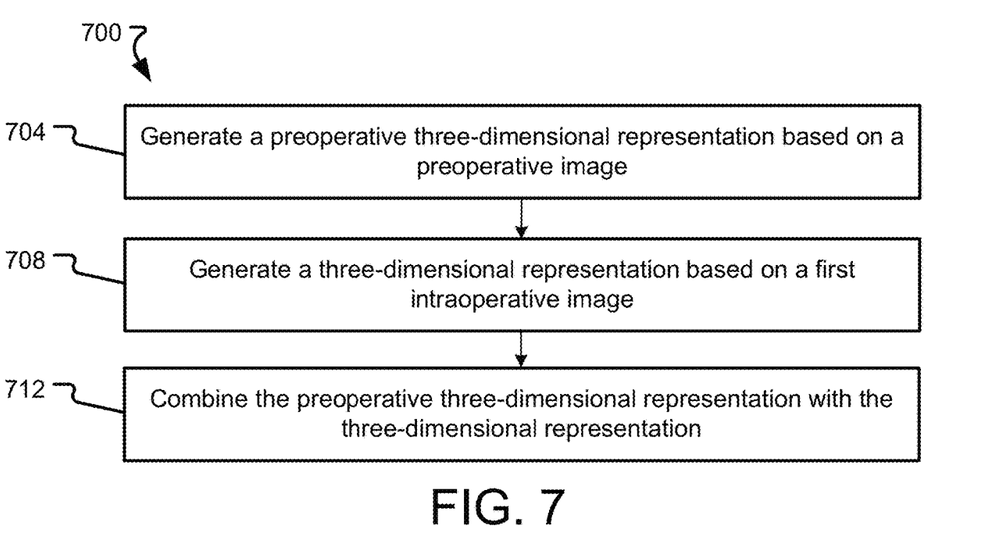
FIG. 7 is a flowchart according to at least one embodiment of the present disclosure.

FIG. 7 depicts a method 700 that may be used, for example, for generating a hybrid three-dimensional representation.

The method 700 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 700. The at least one processor may perform the method 700 by executing instructions stored in a memory such as the memory 106. The instructions may correspond to one or more steps of the method 700 described below. The instructions may cause the processor to execute one or more algorithms, such as the algorithm 120.

The method 700 comprises generating a preoperative three-dimensional representation (step 704). The preoperative three-dimensional representation may be generated based on one or more preoperative image(s) such as the preoperative image 202. The preoperative image may be received, for example, at step 504 of method 500 described above. Pose information corresponding to a pose of an imaging device such as the imaging device 112 when each preoperative image was obtained may also be used in generating the preoperative three-dimensional representation. The preoperative three-dimensional representation may depict one or more anatomical elements.

The method 700 also comprises generating a three-dimensional representation (step 708). The step 708 may be the same as or similar to the step 704 with respect to generating a three-dimensional representation. The three-dimensional representation may be generated based on intraoperative images received, for example, at steps 508 and/or 520 of method 500 described above. The three-dimensional representation may depict one or more anatomical elements. At least one of the one or more anatomical elements of the three-dimensional representation may be the same as the one or more anatomical elements depicted by the preoperative three-dimensional representation.

The method 700 also comprises combining the preoperative three-dimensional representation and the three-dimensional representation (step 712). Combining the preoperative three-dimensional representation and the three-dimensional representation may form a hybrid three-dimensional representation. The hybrid three-dimensional representation may comprise the preoperative three-dimensional representation and the three-dimensional representation overlaid, integrated, merged, or otherwise combined with each other. For example, a three-dimensional representation of a tumor may be generated based on the intraoperative images. The three-dimensional representation of the tumor may be overlaid onto a preoperative three-dimensional representation of an organ generated based on the preoperative images.

It will be appreciated that a navigation system such as the navigation system 118 may use the hybrid three-dimensional representation for navigation. It will also be appreciated that the hybrid three-dimensional representation may be updated in the same or similar manner as the hybrid image described above with respect to FIGS. 4 and 4 and methods 500 and 500, respectively. More specifically, an updated three-dimensional representation may be generated based on one or more updated intraoperative images. The updated three-dimensional representation may be combined with the preoperative three-dimensional representation and may replace the initial three-dimensional representation.

The present disclosure encompasses embodiments of the method 700 that comprise more or fewer steps than those described above, and/or one or more steps that are different than the steps described above.

It will be appreciated that any of the steps of methods 400, 500, 600, and/or 700 may be combined in any order. For example, some steps of method 400 and some steps of method 600 may be combined and executed. As noted above, the present disclosure encompasses methods with fewer than all of the steps identified in FIGS. 4-7 (and the corresponding description of the methods 400, 500, 600, 700), as well as methods that include additional steps beyond those identified in FIGS. 4-7 (and the corresponding description of the methods 400, 500, 600, 700). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for generating a hybrid image comprising:
   an imaging device;
   a processor; and
   a memory storing data for processing by the processor, the data, when processed, causing the processor to:
      receive a preoperative image depicting at least one anatomical element;
      receive a first intraoperative image from the imaging device depicting the at least one anatomical element;
      input the preoperative image and the first intraoperative image into a hybrid model, the hybrid model configured to combine the first intraoperative image with the preoperative image;
      generate, with an output of the hybrid model, a hybrid image comprising the preoperative image combined with the first intraoperative image;
      receive pose information of the imaging device, the pose information correlating to one or more poses of the imaging device when the first intraoperative image was obtained;
      generate a three-dimensional representation of the at least one anatomical element based on the preoperative image, the first intraoperative image, and the pose information, the three-dimensional representation including a pose of the at least one anatomical element;
      receive a second intraoperative image;
      detect movement in the at least one anatomical element based on a difference in the first intraoperative image and the second intraoperative image; and
      update the pose of the at least one anatomical element in the three-dimensional representation when movement is detected in the at least one anatomical element.

2. The system of claim 1, wherein the preoperative image comprises an x-ray image and the first intraoperative image comprises an ultrasound image.

3. The system of claim 1, wherein the memory stores further data for processing by the processor that, when processed, causes the processor to:
   input the preoperative image and the second intraoperative image into the hybrid model; and
   generate, with an output of the hybrid model, an updated hybrid image comprising the preoperative image and the second intraoperative image, wherein the second intraoperative image replaces the first intraoperative image.

4. The system of claim 3, wherein the preoperative image, the first intraoperative image, and the second intraoperative image each depict at least one anatomical element, wherein the memory stores further data for processing by the processor that, when processed, causes the processor to:
   detect movement in the at least one anatomical element based on a difference in the first intraoperative image and the second intraoperative image; and
   replace the first intraoperative image with the second intraoperative image when movement is detected.

5. The system of claim 1, wherein the memory stores further data for processing by the processor that, when processed, causes the processor to:
   generate a preoperative three-dimensional representation of one or more anatomical elements using the preoperative image;
   and
   combine the preoperative three-dimensional representation with the three-dimensional representation.

6. The system of claim 1, further comprising a navigation system configured to use the hybrid image for navigation of at least one surgical instrument, wherein the memory stores further data for processing by the processor that, when processed, causes the processor to:
   generate instructions for navigating the at least one surgical instrument based on the hybrid image.

7. The system of claim 1, wherein the hybrid image is generated by at least one of merging the first intraoperative image with the preoperative image or the first intraoperative image is overlaid onto the preoperative image.

8. The system of claim 1, wherein the hybrid model is trained using historical preoperative images and historical intraoperative images.

9. The system of claim 1, wherein the preoperative image comprises hard tissue information and the first intraoperative image comprises soft tissue information, wherein a first set of pixels represents the hard tissue information and a second set of pixels represents the soft tissue information.

10. A device for generating a hybrid image comprising:
    a processor; and
    a memory storing data for processing by the processor, the data, when processed, causing the processor to:
    receive a preoperative image depicting at least one anatomical element;
    receive a first intraoperative image depicting the at least one anatomical element;
    input the preoperative image and the first intraoperative image into a hybrid model, the hybrid model configured to combine the first intraoperative image with the preoperative image;
    generate, with an output of the hybrid model, a hybrid image comprising the preoperative image and the first intraoperative image;
    receive pose information of the imaging device, the pose information correlating to one or more poses of the imaging device when the first intraoperative image was obtained;
    generate a three-dimensional representation of the at least one anatomical element based on the preoperative image, the first intraoperative image, and the pose information, the three-dimensional representation including a pose of the at least one anatomical element;
    receive a second intraoperative image;
    detect movement in the at least one anatomical element based on a difference in the first intraoperative image and the second intraoperative image; and
    update the pose of the at least one anatomical element in the three-dimensional representation when movement is detected in the at least one anatomical element.

11. The device of claim 10, wherein the preoperative image comprises an x-ray image and the first intraoperative image comprises an ultrasound image.

12. The device of claim 10, wherein the memory stores further data for processing by the processor that, when processed, causes the processor to:
    input the preoperative image and the second intraoperative image into the hybrid model; and
    generate an updated hybrid image comprising the preoperative image and the second intraoperative image.

13. The device of claim 12, wherein the preoperative image, the first intraoperative image, and the second intraoperative image each depict at least one anatomical element, wherein the memory stores further data for processing by the processor that, when processed, causes the processor to:
    detect movement in the at least one anatomical element based on a difference in the first intraoperative image and the second intraoperative image.

14. The device of claim 10, wherein the memory stores further data for processing by the processor that, when processed, causes the processor to:
    generate a preoperative three-dimensional representation of one or more anatomical elements using the preoperative image;
    and
    combine the three-dimensional representation with the preoperative three-dimensional representation.

15. The device of claim 10, wherein the hybrid image is generated by at least one of merging the first intraoperative image with the preoperative image or the first intraoperative image is overlaid onto the preoperative image.

16. The device of claim 10, wherein the hybrid model is trained using historical preoperative images and historical intraoperative images.

17. The device of claim 10, wherein the preoperative image comprises hard tissue information and the first intraoperative image comprises soft tissue information.

18. A system for navigating using a hybrid image comprising:
    an imaging device;
    a navigation system;
    a processor; and
    a memory storing data for processing by the processor, the data, when processed, causing the processor to:
    receive a preoperative image depicting at least one anatomical element;
    receive an intraoperative image from the imaging device depicting the at least one anatomical element;
    input the preoperative image and the first intraoperative image into a hybrid model, the hybrid model configured to combine the first intraoperative image with the preoperative image;
    generate, with the output of the hybrid model, a hybrid image comprising the preoperative image and the first intraoperative image;
    receive pose information of the imaging device, the pose information correlating to one or more poses of the imaging device when the first intraoperative image was obtained;
    generate a three-dimensional representation of the at least one anatomical element based on the preoperative image, the first intraoperative image, and the pose information, the three-dimensional representation including a pose of the at least one anatomical element;
receive a second intraoperative image;
detect movement in the at least one anatomical element based on a difference in the first intraoperative image and the second intraoperative image; and
update the pose of the at least one anatomical element in the three-dimensional representation when movement is detected in the at least one anatomical element.

\* \* \* \* \*